(12) United States Patent
Montana

(10) Patent No.: US 9,744,011 B2
(45) Date of Patent: Aug. 29, 2017

(54) DENTAL CLEANING SYSTEM AND METHOD OF USING SAME

(71) Applicant: Mark Montana, Tempe, AZ (US)

(72) Inventor: Mark Montana, Tempe, AZ (US)

(73) Assignee: Mark Montana, Tempe, AZ (US)

( * ) Notice: Subject to any disclaimer, the term of this patent is extended or adjusted under 35 U.S.C. 154(b) by 46 days.

(21) Appl. No.: 14/679,744

(22) Filed: Apr. 6, 2015

(65) Prior Publication Data

US 2016/0287362 A1  Oct. 6, 2016

(51) Int. Cl.
| | |
|---|---|
| *A61C 17/00* | (2006.01) |
| *A61C 17/26* | (2006.01) |
| *A61C 17/22* | (2006.01) |
| *A61C 8/00* | (2006.01) |
| *A61C 13/225* | (2006.01) |

(52) U.S. Cl.
CPC ............ *A61C 17/036* (2013.01); *A61C 8/005* (2013.01); *A61C 17/00* (2013.01); *A61C 17/222* (2013.01); *A61C 17/26* (2013.01); *A61C 13/225* (2013.01)

(58) Field of Classification Search
CPC ..... A61C 17/036; A61C 17/222; A61C 17/26; A61C 8/048
USPC ......................................................... 433/125
See application file for complete search history.

(56) References Cited

U.S. PATENT DOCUMENTS

| | | | |
|---|---|---|---|
| 3,088,150 A | 5/1963 | Sweeney | |
| 4,301,567 A | 11/1981 | Tucker | |
| 4,941,227 A | 7/1990 | Sussman | |
| 5,067,195 A | 11/1991 | Sussman | |
| 5,797,744 A | 8/1998 | Rosenberg | |
| 5,940,923 A | 8/1999 | Gunning | |
| 6,030,219 A | 2/2000 | Zuest et al. | |
| 8,739,350 B1 | 6/2014 | Lackenbauer | |
| 2008/0076091 A1 | 3/2008 | Moreschini | |
| 2011/0067194 A1* | 3/2011 | Al-Qaffas | A46B 9/045 15/167.2 |

FOREIGN PATENT DOCUMENTS

| | | |
|---|---|---|
| EP | 2845563 | 11/2015 |
| WO | 2013060563 | 5/2013 |

* cited by examiner

*Primary Examiner* — Paula J Stice
(74) *Attorney, Agent, or Firm* — Duane Morris LLP; Gregory M. Lefkowitz

(57) ABSTRACT

A dental cleaning system includes a cylindrical body with a first portion and a second portion. A cleaning portion is positioned within the second portion and includes a cavity to enable the cleaning portion to at least partially enclose a dental implant device. The cylindrical body rotates such that the cleaning portion therein rotates to clean at least a portion of the dental implant device. A projection extends outwardly from a surface of the cleaning portion such that the projection is positioned within the cavity. The projection removes debris from at least a portion of the dental implant device when the cylindrical body rotates. A plurality of cleaning protrusions extend outwardly from a sidewall of the cavity such that the cleaning protrusions at least partially circumscribe the projection. The cleaning protrusions remove the debris from at least a portion of the dental implant device when the cylindrical body rotates.

13 Claims, 12 Drawing Sheets

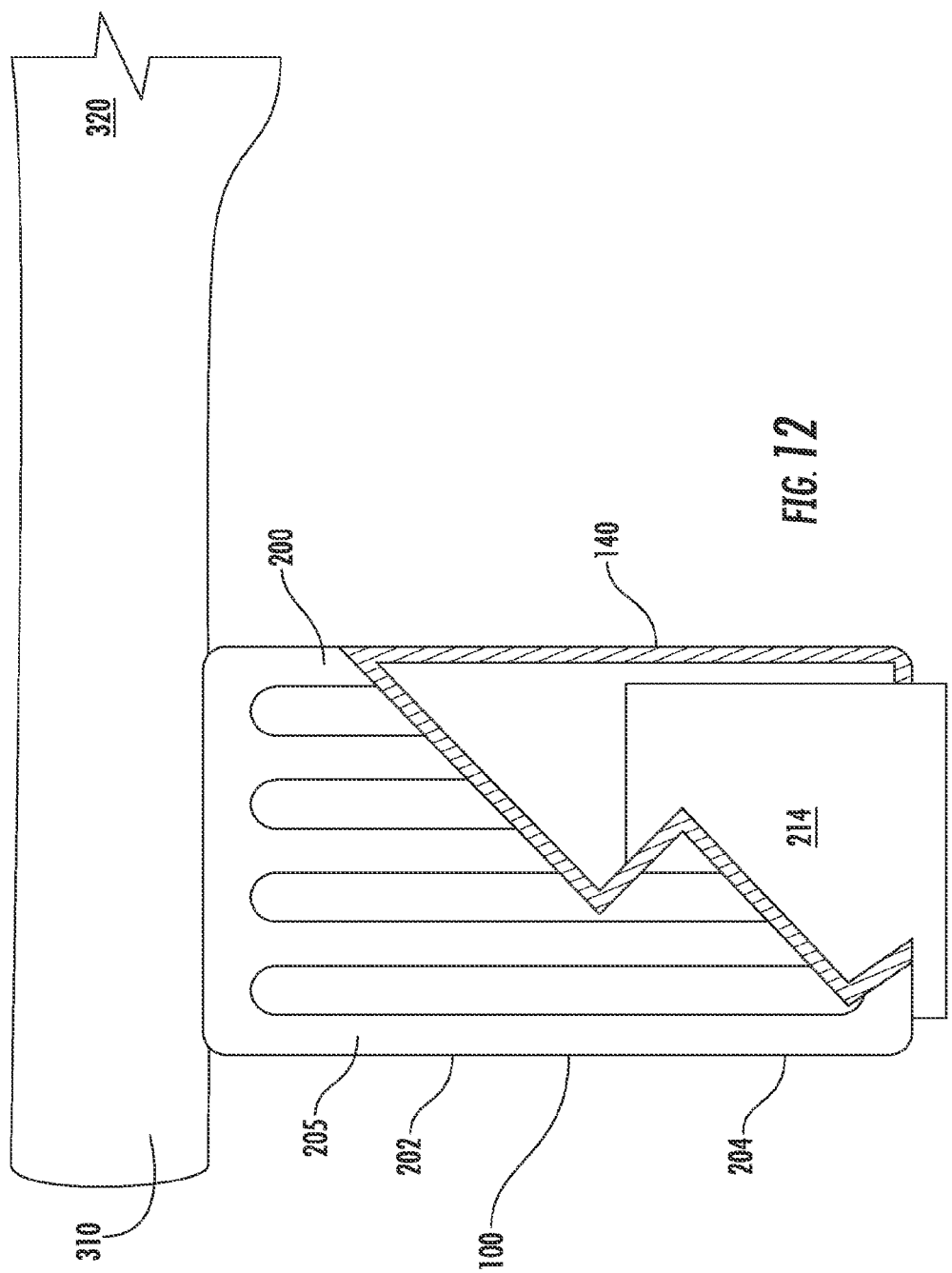

US 9,744,011 B2

DENTAL CLEANING SYSTEM AND METHOD OF USING SAME

BACKGROUND

Dental implants or dental implant devices have become increasingly popular as an alternative to traditional complete dentures and removable partial dentures. Many known dental implant devices may be used to greatly enhance the functionality and comfort of complete dentures in an individual's mouth. At least some known dental implant devices can be placed into the bone and, in less than six months, the implants can be used to retain, stabilize and support dental prosthesis within the mouth. At least some known dental implant devices can include an over-denture abutment or stud abutment or solitary anchor that is attached to the dental implant post and serves as a connector for the denture. At least some known over-denture abutments are small, free-standing cylindrical devices that are connected to the dental implant post. The denture can be secured by means of a resilient attachment that is configured to snap into, onto or around the abutment.

Accumulation of debris into or onto the over-denture abutment can occur and such accumulation of debris can reduce the effectiveness of the attachment apparatus. As such, the over-denture abutment can be cleaned by a user to prevent plaque accumulation and possible bone loss, as well as to assure the denture is properly secured. At least some known over-denture abutments can be cleaned using known dental cleaning tools, such as toothbrushes. However, such known cleaning tools are designed to clean teeth or tooth-like shapes and are not intended to clean the outer and inner surfaces of small cylinders or other retentive shapes. Moreover, many users of dental implant devices, such as dental implant over-dentures, are elderly and/or may suffer from vision or dexterity loss. As such, cleaning the over-denture abutment using at least some known dental cleaning tools can be challenging.

BRIEF DESCRIPTION

The embodiments described herein provide a dental cleaning system that can be used with dental assemblies for efficiently and conveniently cleaning at least a portion of dental implant devices, such as an over-denture abutment. For example, in one embodiment, a dental cleaning system is provided that includes a cylindrical body that includes a first portion and a second portion. A cleaning portion is positioned within the second portion of the cylindrical body, wherein the cleaning portion includes a cavity defined therein to enable the cleaning portion to at least partially enclose a dental implant device, such as an over-denture abutment, therein. The cylindrical body is configured to rotate such that the cleaning portion therein rotates to facilitate cleaning at least a portion of the dental implant device. A projection extends outwardly from a surface of the cleaning portion such that the projection is positioned within the cavity. The projection is configured to remove debris from at least a portion of the interior of the dental implant device when the cylindrical body is being rotated. A plurality of cleaning protrusions each extends outwardly from a sidewall of the cavity such that the cleaning protrusions at least partially circumscribe the projection positioned within the cavity. The cleaning protrusions are configured to remove the debris from at least a portion of the exterior of the dental implant device when the cylindrical body is being rotated.

In another embodiment, a method of using a dental cleaning system is provided. The method includes providing a cylindrical body that includes a first portion and a second portion. A cleaning portion is positioned within the second portion of the cylindrical body, wherein the cleaning portion includes a cavity defined therein and includes a projection that extends outwardly from a surface of the cleaning portion such that the projection is positioned within the cavity. The cleaning portion further includes a plurality of cleaning protrusions that each extends outwardly from a sidewall of the cavity such that the cleaning protrusions at least partially circumscribe the projection positioned within the cavity. At least a portion of a dental implant device, such as an over-denture abutment, is enclosed within the cavity. The method includes rotating the cylindrical body such that the cleaning portion therein is being rotated to clean at least a portion of the dental implant device within the cavity. The projection is used when the cylindrical body is being rotated to remove debris from at least a portion of the dental implant device. The cleaning protrusions are also used when the cylindrical body is being rotated to remove the debris from at least a portion of the dental implant device.

In yet another embodiment, a dental assembly is provided and includes a main body that includes a first end and a second end. A coupling member is coupled to the first end of the main body, wherein the coupling member is configured to couple the first end of the main body to an end portion of a tooth cleaner. A dental cleaning system is configured to be positioned within an opening defined within the second end of the main body. The dental cleaning system includes a cylindrical body that includes a first portion and a second portion. A cleaning portion is positioned within the second portion of the cylindrical body, wherein the cleaning portion includes a cavity defined therein to enable the cleaning portion to at least partially enclose a dental implant device, such as an over-denture abutment, therein. The cylindrical body is configured to be rotated such that the cleaning portion therein rotates to facilitate cleaning at least a portion of the dental implant device. A projection extends outwardly from a surface of the cleaning portion such that the projection is positioned within the cavity, wherein the projection is configured to remove debris from at least a portion of the interior of the dental implant device when the cylindrical body is rotated. A plurality of cleaning protrusions each extends outwardly from a sidewall of the cavity such that the cleaning protrusions at least partially circumscribe the projection positioned within the cavity. The cleaning protrusions are configured to remove the debris from at least a portion of the exterior of the dental implant device when the cylindrical body is being rotated.

BRIEF DESCRIPTION OF THE DRAWINGS

FIG. 12 is a side, cut-away view of a dental assembly coupled to a cleaning head and electrical handle as described herein.

DETAILED DESCRIPTION

Figure 1:
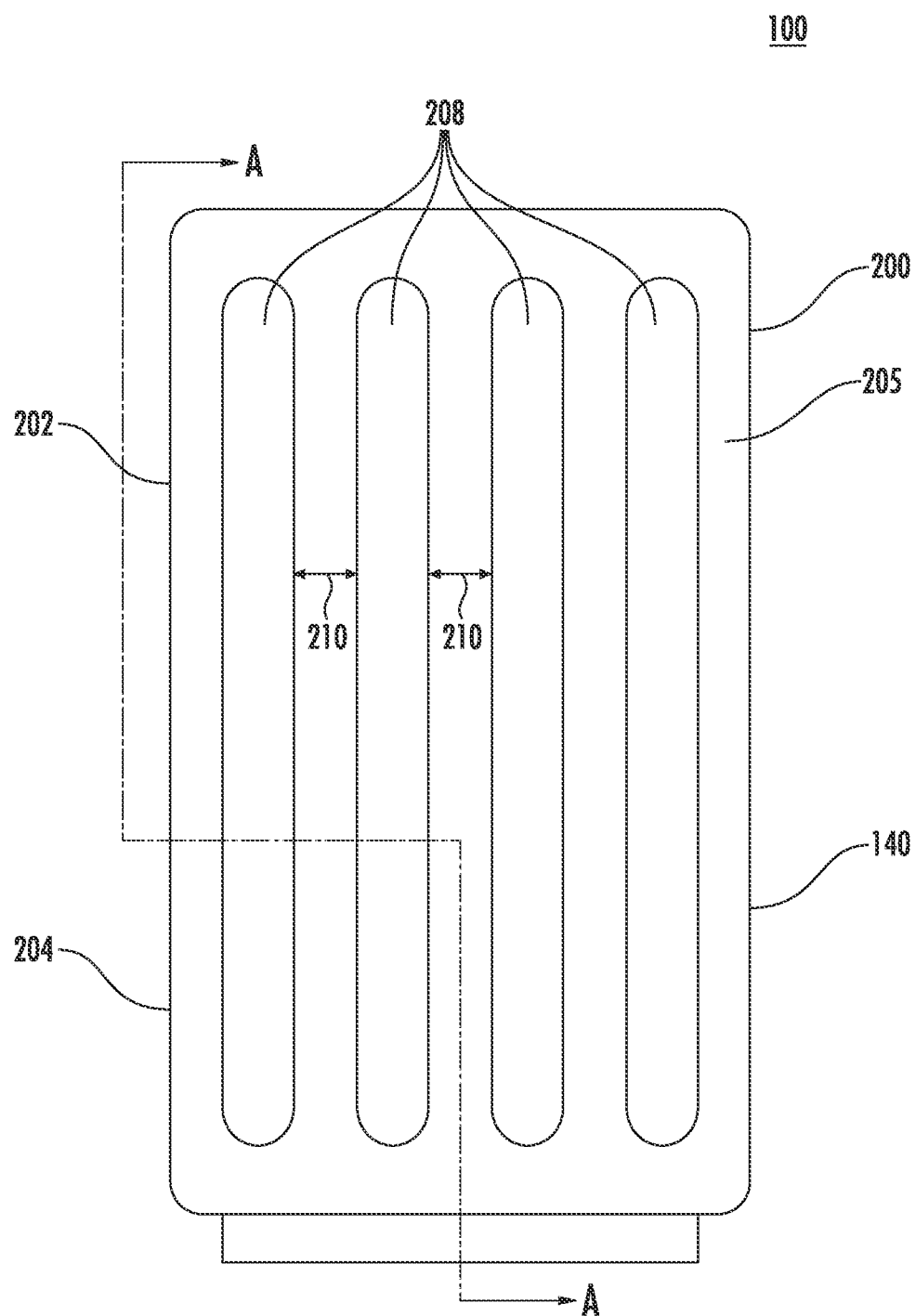
FIG. 1 is a side view of a dental assembly as described herein.

FIGS. 1-12 illustrate a dental assembly 100 that includes a generally cylindrical body 102 and a dental cleaning system 140 housed therein. As described in more detail below the dental assembly 100 is particularly adapted for cleaning dental abutments, such as the one shown in U.S. Pat. No. 6,030,219 by Zuest and Mullaly. Food, bacteria, and other debris can collect in such dental abutments. However, existing oral care techniques, such as toothbrushes and water flossers, may not adequately clean these dental abutments, which can lead to halitosis and disease.

In some embodiments, the dental cleaning system 140 includes a cylindrical body 200 having an upper or first portion 202 and a bottom or second portion 204. In some embodiments, the cylindrical body 200 has an exterior surface 205 that includes a shell fabricated from a suitable lightweight and rigid material, such as a metal or rigid plastic material. Moreover, in some embodiments, exterior surface 205 is configured to enable a user to grip and rotate cylindrical body 200. For example, in some embodiments, exterior surface 205, includes a plurality of grooves 208 within first portion 202 such that each groove 208 is positioned a predefined distance 210 from an adjacent groove 208. Distance 210 can be any suitable distance that enables cylindrical body 200 and/or dental cleaning system 140 to function as described herein.

Figure 2:
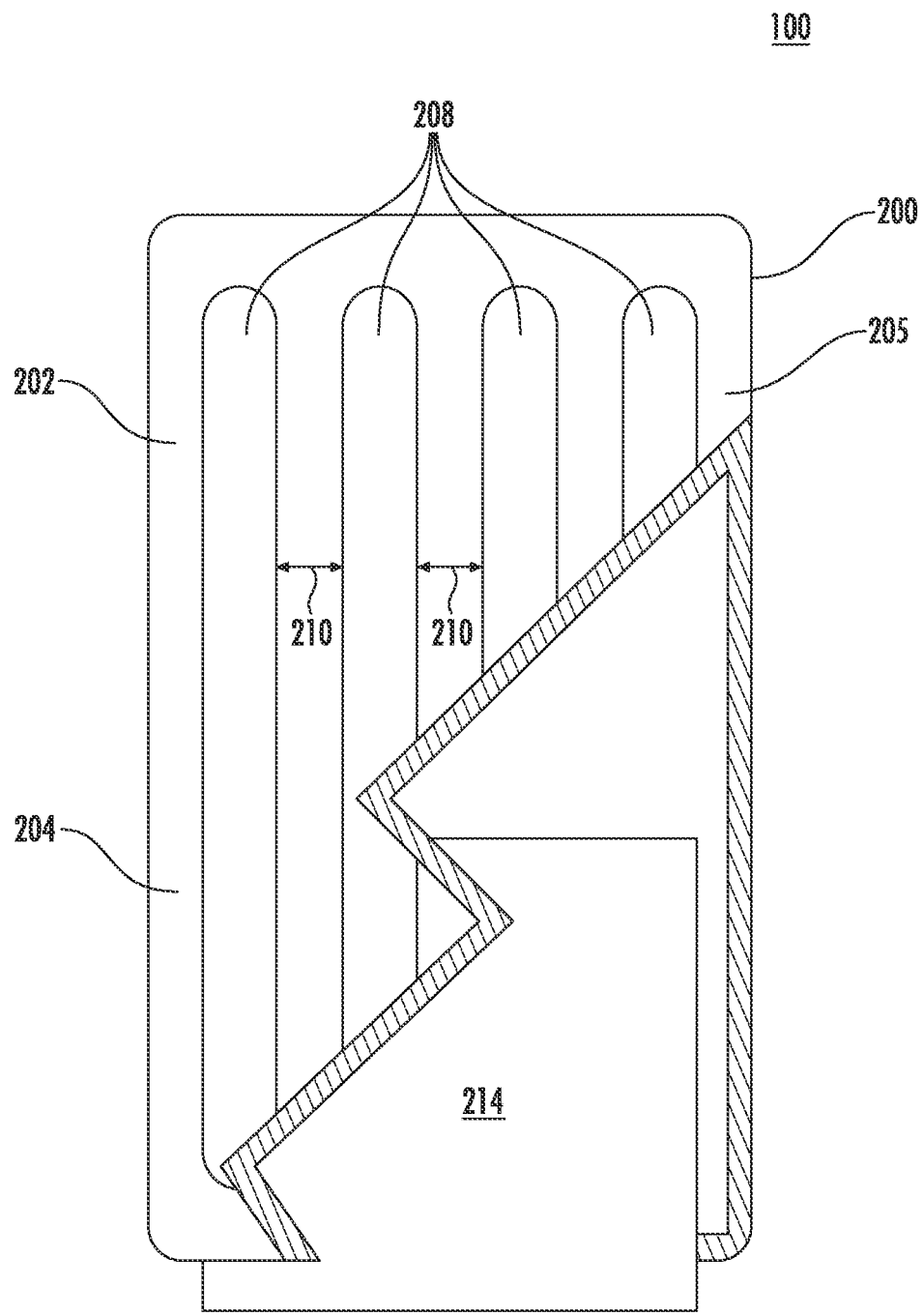
FIG. 2 is a side, cut-away view of a dental assembly having one cleaning portion as described herein.
Figure 3:
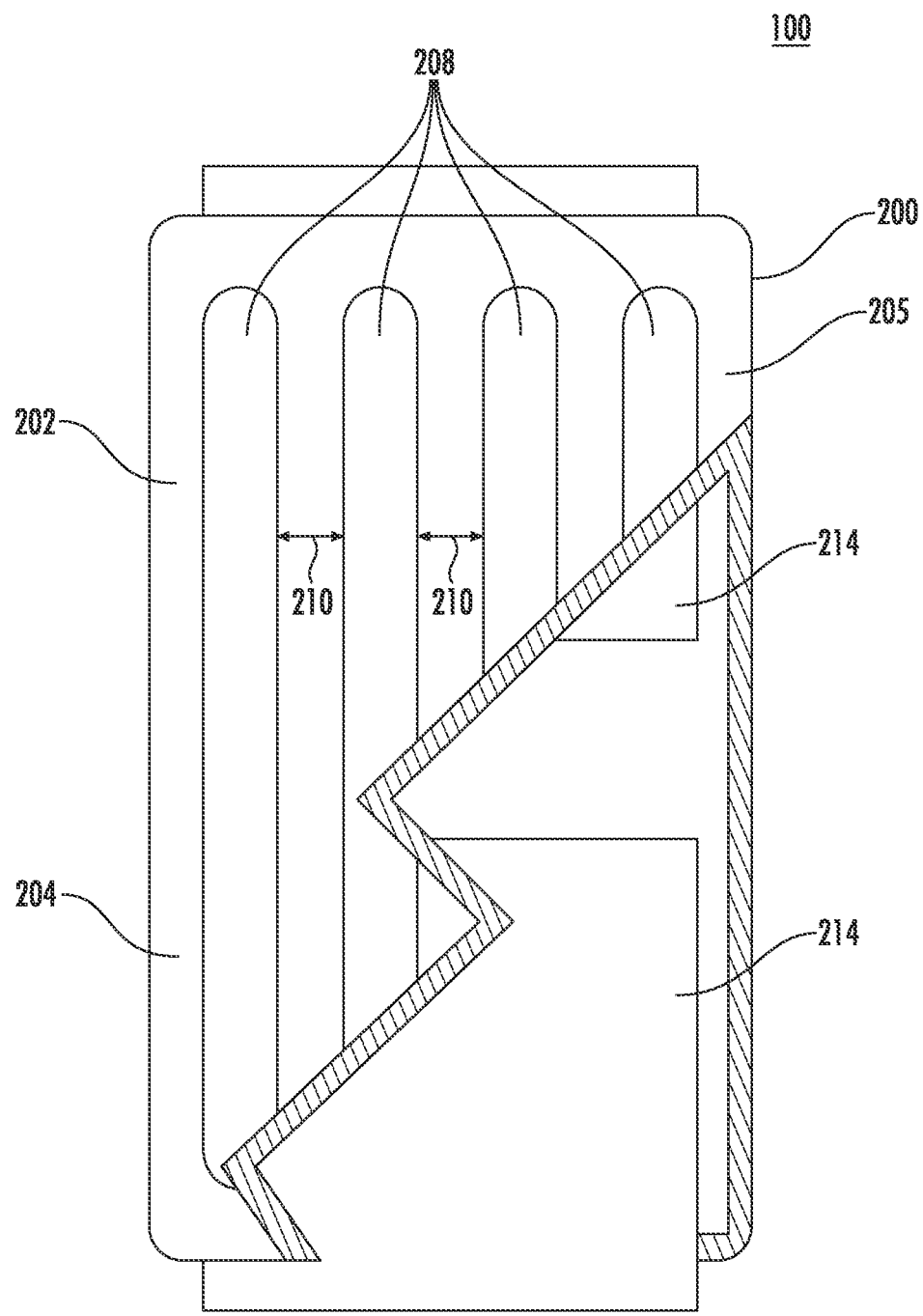
FIG. 3 is a side, cut-away view of a dental assembly having two cleaning portions as described herein.

In some embodiments, as shown in FIGS. 2 and 3, the bottom portion 204 of cylindrical body 200 is sized and configured such that a cleaning portion 214 can be positioned within second portion 204. In some embodiments, as shown in FIG. 3, both the top portion 202 and the bottom portion 204 are sized and configured such that a cleaning portion 214 can be positioned therein. In some embodiments, cleaning portion 214 can be removably coupled within second portion 204 of cylindrical body 200. In other embodiments, cleaning portion 214 can be integrally formed within second portion 204 of cylindrical body 200. In some embodiments, cleaning portion 214 is formed of a suitable resilient material including, but not limited to, natural or synthetic rubber, silicone, nylon, elastomers, and other polymers.

Figure 6:
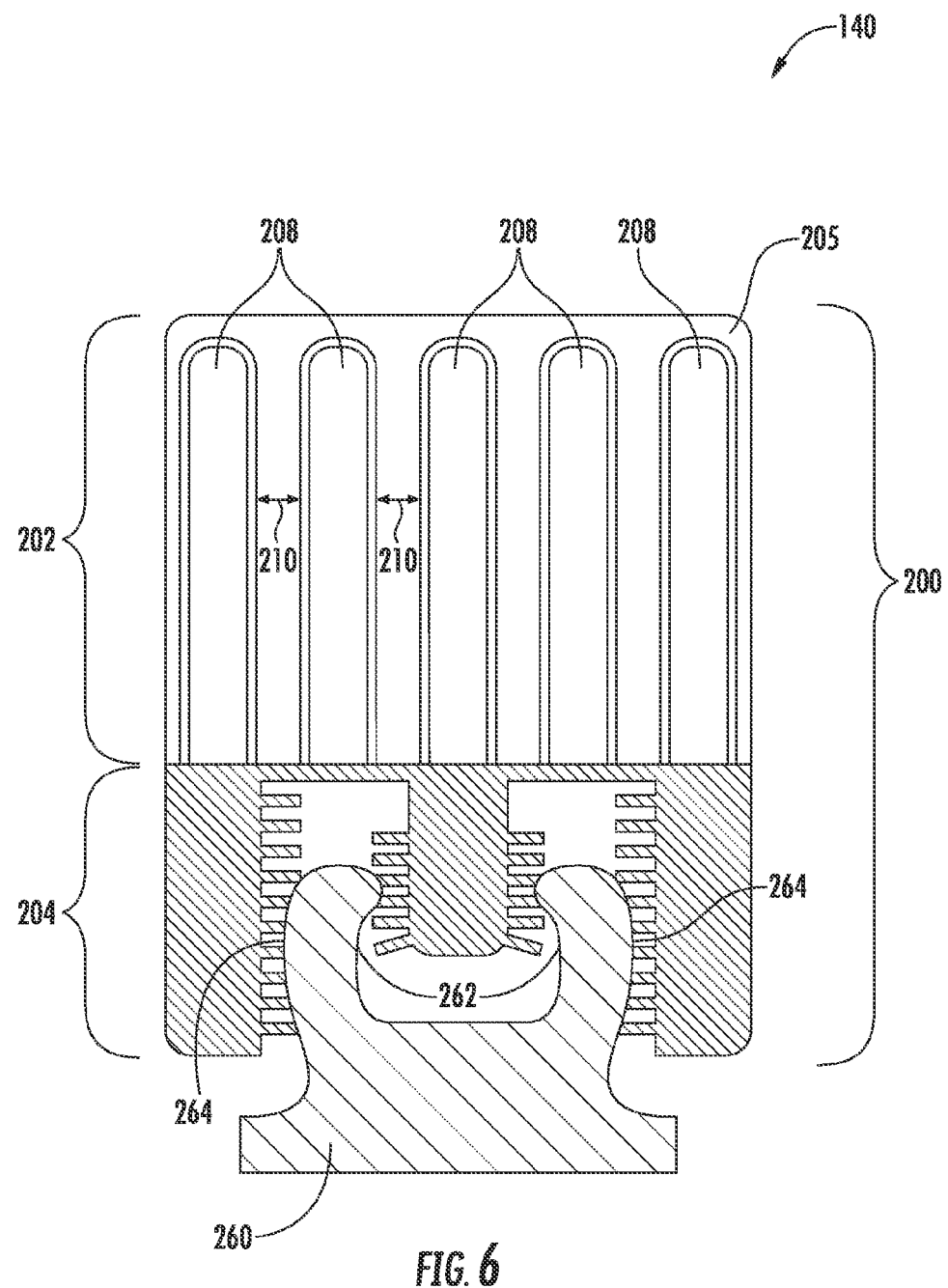
FIG. 6 is a cross-sectional view of the dental assembly of FIG. 5 placed over a dental implant.
Figure 9:
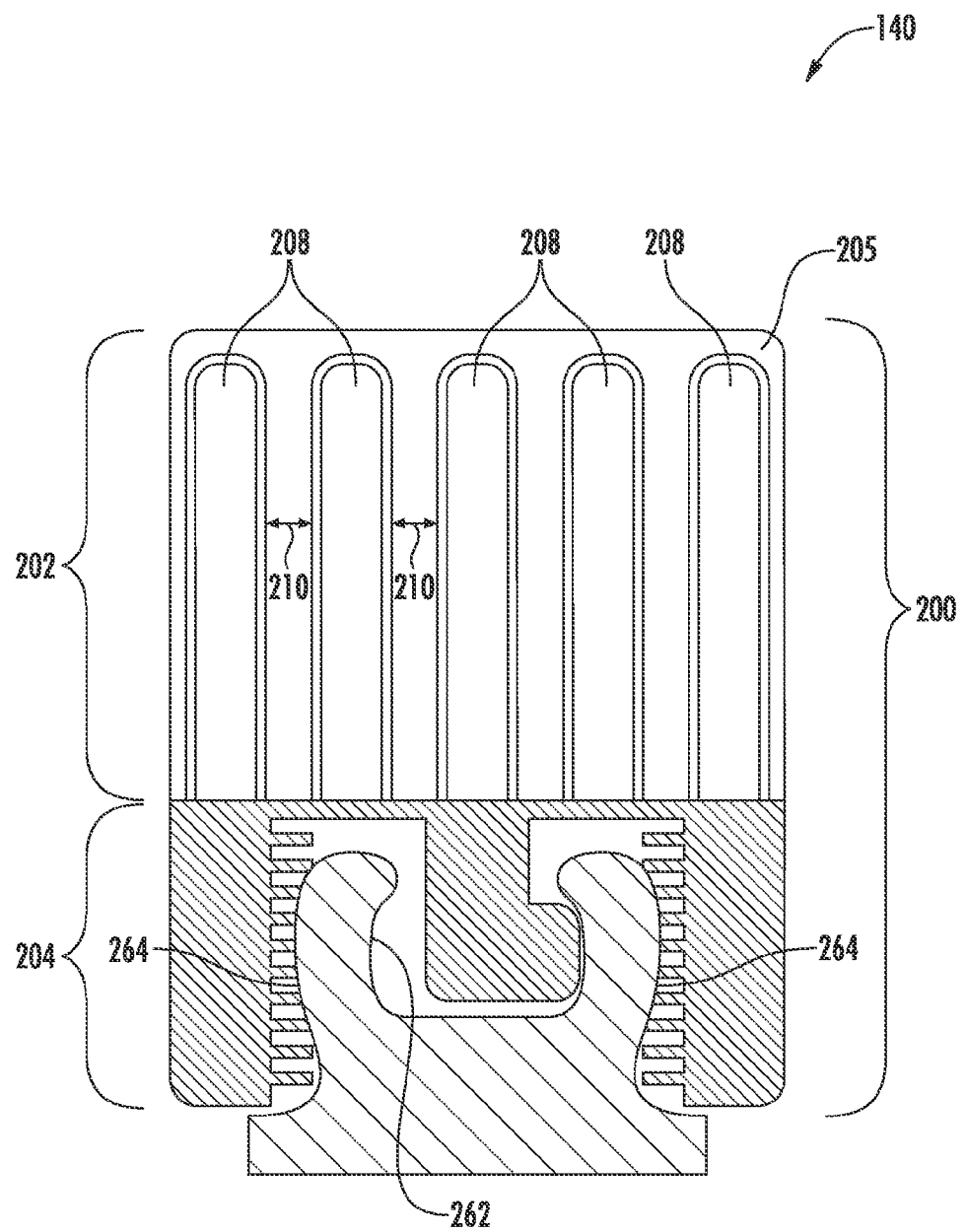
FIG. 9 is a cross-sectional view of the dental assembly of FIG. 8 placed over a dental implant.

As shown in FIGS. 6 & 9, in some embodiments, the cleaning portion 214 includes a cavity 216 defined therein to enable cleaning portion 214 to receive at least a portion of a dental implant 260 therein. For example, in some embodiments, cavity 216 is sized and configured to receive a portion of an over-denture abutment as shown in FIGS. 6 & 9.

A projection portion 220 extends outwardly from a top surface 222 of cleaning portion 214 such that projection 220 is positioned within cavity 216. For example, in some embodiments, projection 220 can have a first end 226 that is integrally formed onto top surface 222 using a variety of manufacturing processes known in the art, such as, but not limited to, a molding process, a drawing process, or a machining process. Projection 220 can also have a distal end 228 opposite the first end 226 that is positioned a predefined distance 230 from first end 226.

In some embodiments, the projection 220 includes an exterior surface 234 and one or more cleaning protrusions 236 that each extends radially outward from the exterior surface 234, wherein the cleaning protrusions 236 are configured to remove debris from at least a portion of the dental implant device. For example, cleaning protrusions 236 can be shaped as flexible fingers (FIGS. 5 & 6), fins or blade (FIGS. 8-10), tufts, or other suitable shapes that enable cleaning.

In some embodiments, cavity 216 includes a sidewall 240 and at least one cleaning protrusion 244 that each extends radially inward from sidewall 240 toward the projection 220. In some embodiments, the at least one cleaning protrusions 244 contact the projection 220, while the at least one cleaning protrusions 244 do not contact the projection 220 in other embodiments. The cleaning protrusions 244 can also be configured to remove debris from at least a portion of the dental implant device 260. For example, the cleaning protrusions 244 can also be shaped as flexible fingers, fins or blades, tufts, or other suitable shapes that facilitate cleaning. The cleaning protrusions 236, 244 can be formed of a flexible material adapted to scrape debris off the inner 262 and outer surfaces 264, respectively, of the dental implant device 260.

In some embodiments of the system 140, a cleaning portion 214 is removably positioned within a second portion 204 of cylindrical body 200, before use, while the insert portion 214 is a permanent part of the body 200 in other embodiments. As shown in FIGS. 6 & 9, in use, the cylindrical body 200 can be positioned over a portion of the dental implant device 260 such that the cavity 216 receives at least a portion of the abutment 260 therein. In some embodiments, when the abutment 260 is positioned within cavity 216, the projection 220 will be positioned within an interior portion 262 of the abutment 260 and the cleaning protrusions 244 can contact the exterior portion 264 of the abutment 260.

The cylindrical body 200 can then be rotated either manually or with the assistance of an electric handle so that the cleaning protrusions 236 and 244 effectively scrape and/or scrub the inner and outer surfaces 262, 264 of the dental implant device 260, respectively. When cleaning portion 214 is being rotated, the projection 220 and associated cleaning protrusions 236 rotate to remove debris from the interior portion 262 of the abutment 260. In addition, when cleaning portion 214 is being rotated, the external cleaning protrusions 244 remove debris from the exterior portion 264 of the abutment 260. After the abutment 260 is cleaned, the dental cleaning system 140 can be lifted and removed from covering the abutment within cavity 216. The cylindrical body 200 can then be rinsed and cleaned to remove any debris (e.g., food, plaque, etc.) from the cleaning protrusions 236, 244.

In some embodiments, the user can use the dental cleaning system 140 with dental assembly 100 to clean the abutment 260. For example, in some embodiments, dental cleaning system 140 can enclose the abutment 260 while being positioned within dental assembly 100. As described above, an electronic toothbrush can be coupled to dental assembly 100 to enable rotation or partial rotation of the dental assembly 100. When dental assembly 100 is being rotated by the toothbrush, then dental cleaning system 140 positioned therein rotates. This rotations enables cleaning protrusions 236 to remove debris from the interior portion 262 of the abutment 260 and enables cleaning protrusions 244 to remove debris from the exterior portion 264 of the abutment 260.

Figure 4:
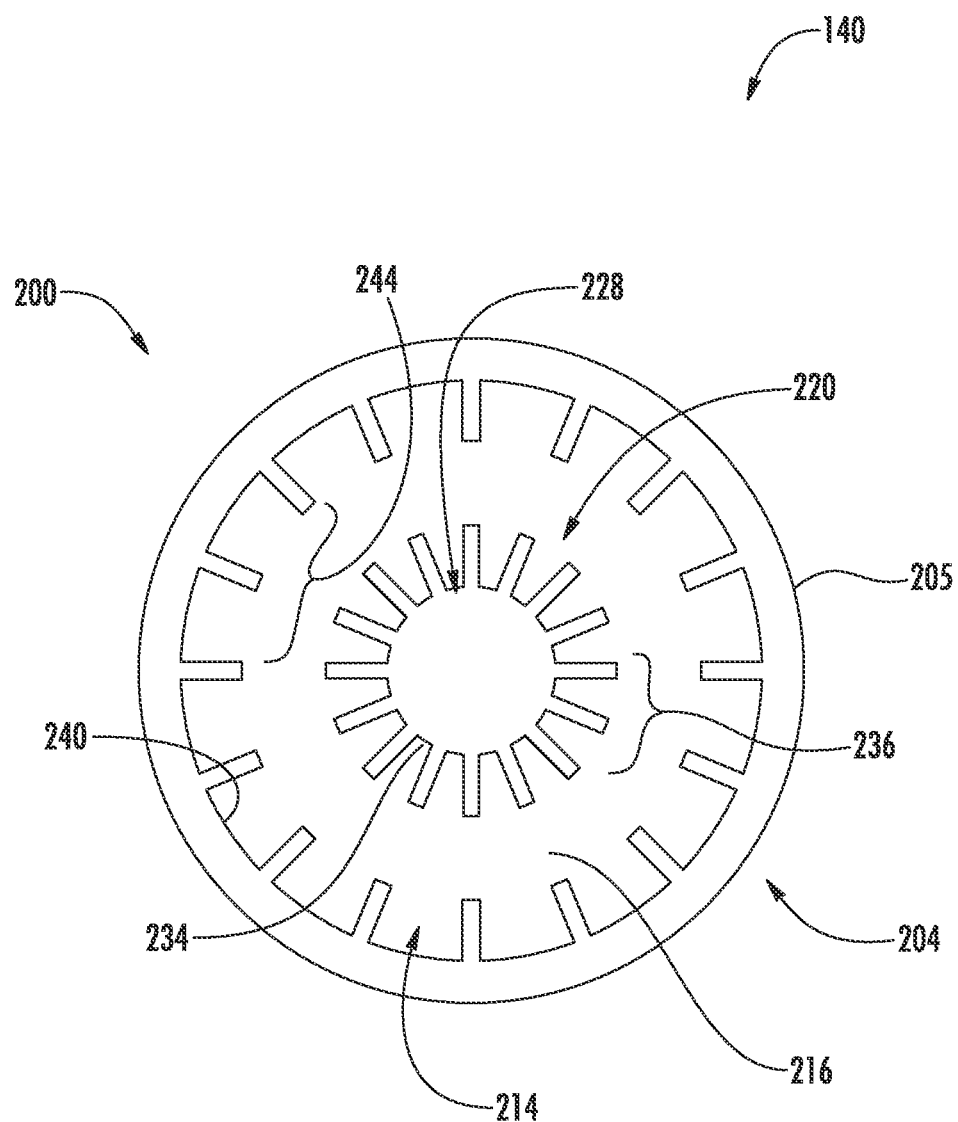
FIG. 4 is a bottom view of one embodiment of a dental assembly as described herein.
Figure 5:
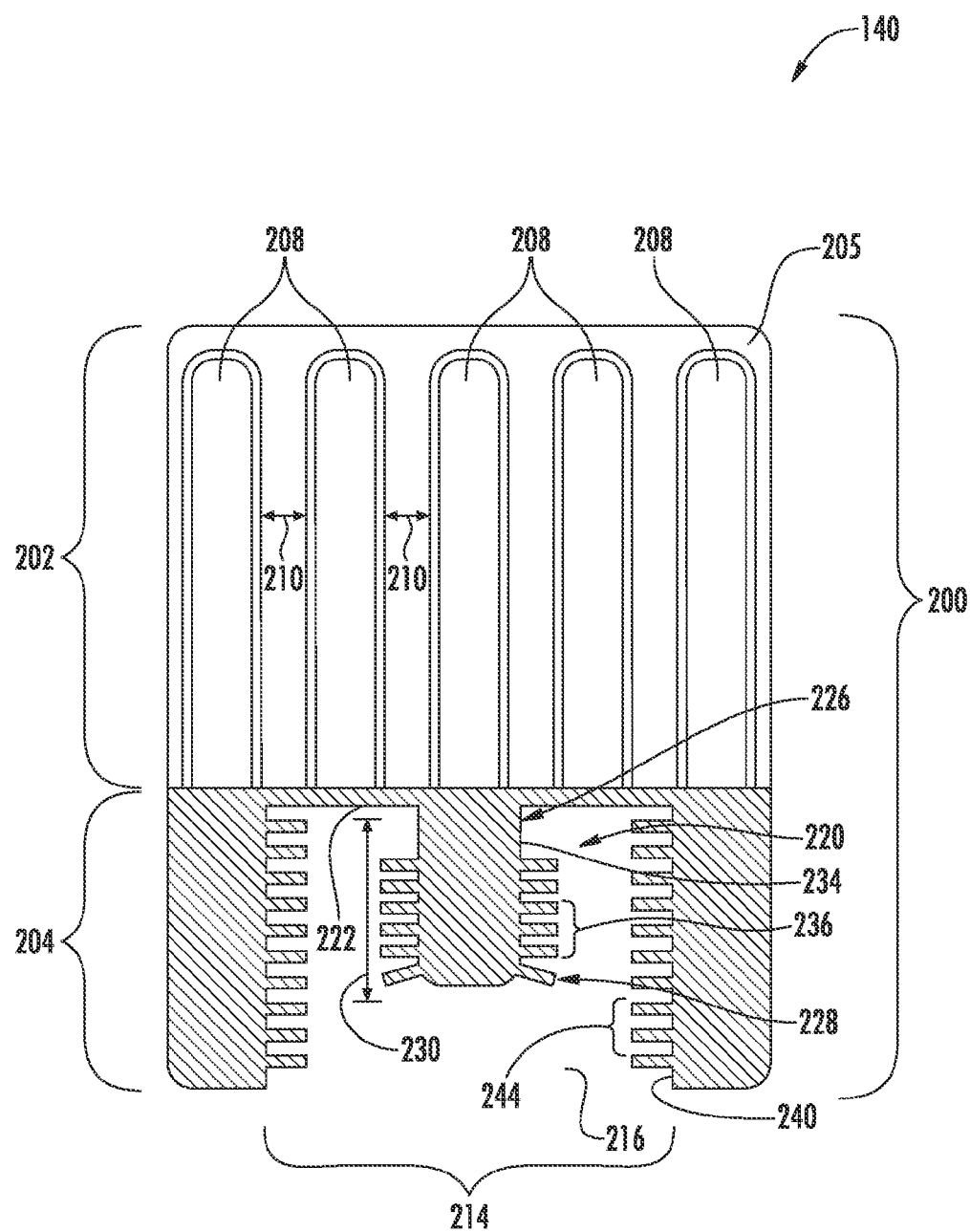
FIG. 5 is a cross-sectional view of the embodiment of FIG. 4 taken along cut line A-A of FIG. 1.
Figure 11:
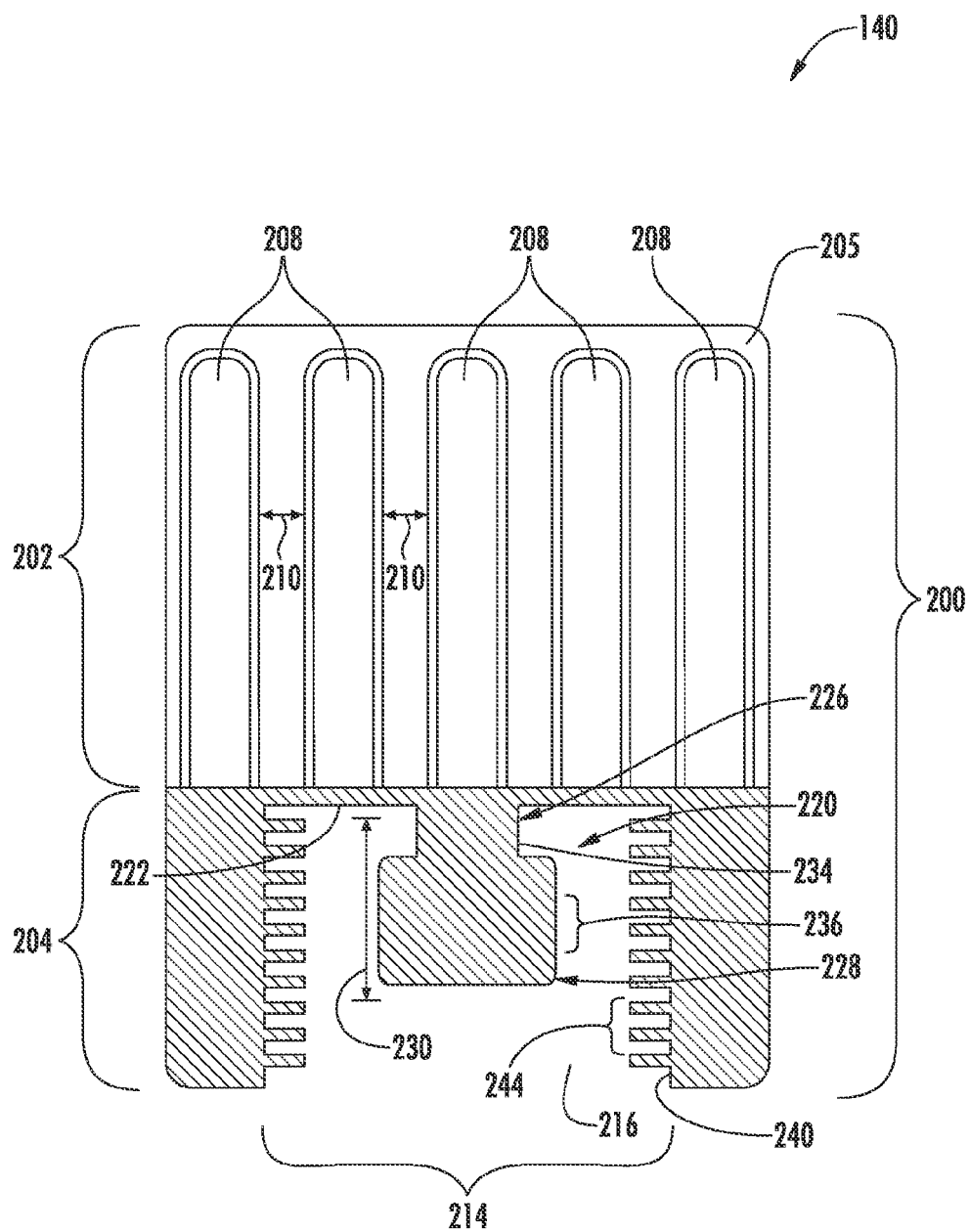
FIG. 11 is an alternate cross-sectional view of the embodiment of FIG. 4 taken along cut line A-A of FIG. 1.

FIG. 4 shows an embodiment with a plurality of inner cleaning protrusions 236 and a plurality of outer cleaning protrusions 244. FIGS. 5 and 6 show cross-sections of the embodiment of FIG. 4 taken along cutline A-A of FIG. 1 where the inner and outer cleaning protrusions 236, 244 are flexible fingers. FIG. 11 shows a cross-section of the embodiment of FIG. 4 taken along cutline A-A of FIG. 1 wherein the inner cleaning protrusions 236 are fins or blades, while the outer cleaning protrusions 244 are flexible fingers.

Figure 7:
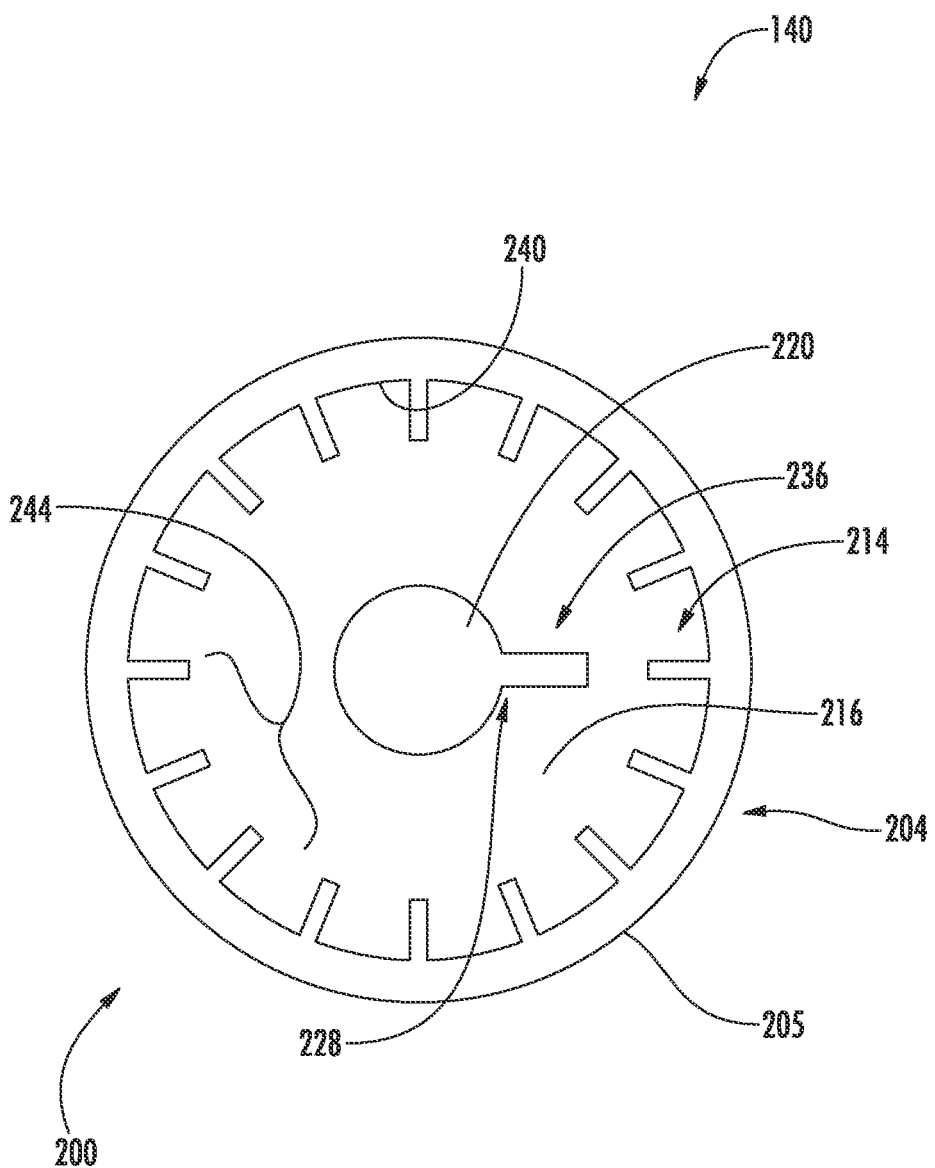
FIG. 7 is a bottom view of an embodiment of a dental assembly as described herein.
Figure 8:
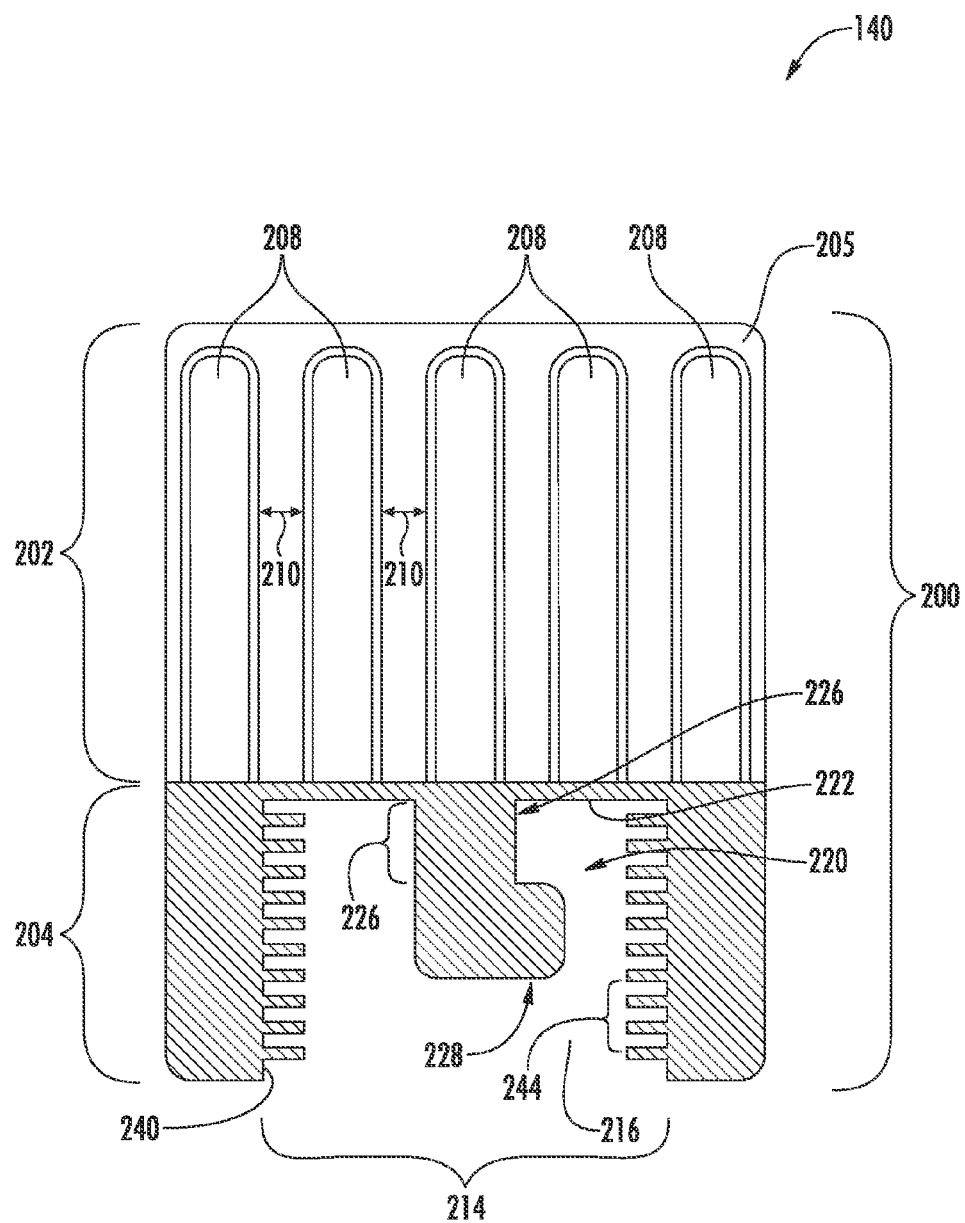
FIG. 8 is a cross-sectional view of the embodiment of FIG. 7 taken along cut line A-A of FIG. 1.
Figure 10:
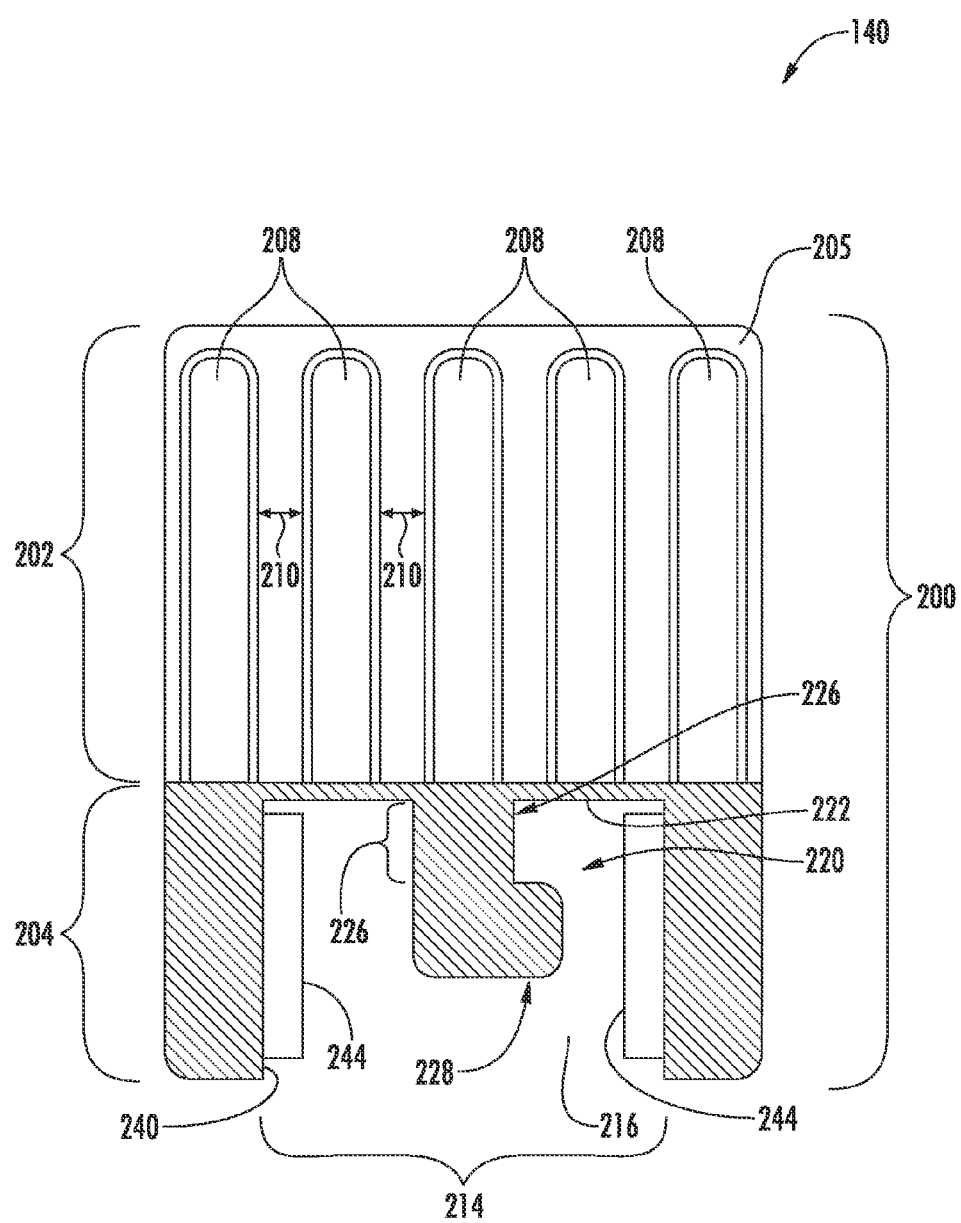
FIG. 10 is an alternate cross-sectional view of the embodiment of FIG. 7 taken along cut line A-A of FIG. 1.

FIG. 7 shows an embodiment with a single inner cleaning protrusion 236 and a plurality of outer cleaning protrusions 244. FIGS. 8 and 9 show cross-sections of the embodiment of FIG. 7 taken along cutline A-A of FIG. 1 where the inner cleaning protrusion 236 is a blade and the outer cleaning protrusions 244 are flexible fingers. In such an embodiment, the inner cleaning protrusion can extend outwardly from the projection 220 proximate the distal end 228. In some embodiments, as evident from FIGS. 7-10, the height (vertical distance) of the inner cleaning protrusion 236 is less than the height (vertical distance) of the protrusion 220. In some such embodiments, as evident from FIGS. 7-10, the projection 220, including the inner cleaning protrusion 236, can have a substantially L-shaped appearance from the side. As will be understood, in some embodiments, the height (vertical distance) of the inner cleaning protrusion 236 is equal to the height (vertical distance) of the protrusion 220. FIG. 10 shows a cross-section of the embodiment of FIG. 7 taken along cutline A-A of FIG. 1 where the inner cleaning protrusion 236 is a blade and the outer cleaning protrusions 244 are fins or blades.

In some embodiments, the dental assembly 100 can be coupled to a cleaning head 310 that is coupled to an electrical handle 320 for electrically imparting rotation to the dental assembly to facilitate cleaning of a dental implant device 260. The cleaning mechanism is as described herein; however, dental assembly 100 is rotated by the electrical handle rather than manually. In some embodiments, the rotation imparted to the dental assembly 100 by the electrical handle 310 can be less than 360°, or less than 270°, less than 180°, less than 120° (i.e., the dental assembly does not rotate continuously in one direction). In some embodiments, the direction of rotation imparted to the dental assembly 100 by the electrical handle 310 can oscillate between clockwise and counter-clockwise.

In some embodiments, the dental assembly 100 can be permanently attached to the cleaning head 310, which can be removably coupled to the electrical handle 320. In other embodiments, the cleaning head 310 can be removably attached to the cleaning head 310, which can be permanently coupled to the electrical handle 320. In some embodiments, the cleaning head 310 and the electrical handle 320 be an integrally formed device.

As compared to known dental cleaning systems, the embodiments described herein provide a dental cleaning system that can be used to efficiently and conveniently clean at least a portion of a dental implant device, such as an over-denture abutment. For example, in some embodiments, the dental cleaning system is configured to at least partially enclose the dental implant device, such as the over-denture abutment, therein. Moreover, the dental cleaning system is configured to rotate to facilitate cleaning at least a portion of the dental implant device enclosed therein. After the dental implant device has been cleaned, the dental cleaning system can be lifted and removed from enclosing the implant device therein.

Exemplary embodiments of apparatus and methods are described above in detail. The apparatus and methods are not limited to the specific embodiments described herein, but rather, components of each apparatus and/or method may be utilized independently and separately from other components described herein. For example, each apparatus may also be used in combination with other apparatuses and is not limited to practice with only apparatuses as described herein. Rather, the exemplary embodiment can be implemented and utilized in connection with many other applications.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A dental system for cleaning a dental implant abutment, comprising:
    a generally cylindrical body comprising a first portion and a second portion; and
    a cleaning portion positioned within said first portion of said cylindrical body, wherein said cleaning portion comprises a cavity having a first opening at a distal end of the first portion, an inner surface opposite said opening, and a continuous sidewall extending from a perimeter of said opening to said inner surface, said sidewall surrounding the cavity,
    a projection extending vertically down from the inner surface of said cavity,
    at least one second cleaning projection extending radially outward from a side of the projection,
    wherein the at least one second cleaning projection (a) is a fin or a blade, or (b) comprises a plurality of cleaning rows and each cleaning row comprises a plurality of additional cleaning protrusions that each extend radially outward from the projection;
    wherein said sidewall comprises a plurality of cleaning protrusions extending inwardly toward a longitudinal axis of the cavity, and
    wherein, when a dental implant with a central cavity is received within said cavity through said first opening, said plurality of cleaning protrusions are adapted for cleaning exterior walls of the dental implant and said at least one second cleaning projection is adapted for cleaning side walls of the central cavity of the dental implant.

2. A dental cleaning system in accordance with claim 1, wherein said cylindrical body comprises an exterior surface configured to enable a user to grip and rotate said cylindrical body.

3. A dental cleaning system in accordance with claim 2, wherein said exterior surface comprises a plurality of grooves.

4. A dental cleaning system in accordance with claim 2, wherein said exterior surface is formed of a rigid material.

5. A dental cleaning system in accordance with claim 1, wherein said cleaning portion is formed of a resilient material.

6. A dental cleaning system in accordance with claim 1, wherein the at least one second cleaning projection (a) is a fin or a blade.

7. A dental cleaning system in accordance with claim 1, wherein the at least one second cleaning projection (b) comprises a plurality of cleaning rows and each cleaning row comprises a plurality of additional cleaning protrusions that each extend radially outward from the projection.

8. A method of using a dental system for cleaning a dental implant abutment, said method comprising:
providing a dental system for cleaning a dental implant abutment according to claim 1;
receiving at least a portion of a dental implant device within the cavity;
rotating the cylindrical body such that the cleaning portion therein is being rotated to clean at least a portion of the dental implant device within the cavity;
removing debris from at least a portion of the dental implant device via the cleaning protrusions when the cylindrical body is being rotated.

9. A method in accordance with claim 8, wherein using the plurality of cleaning protrusions comprises using the plurality of cleaning protrusions when the cylindrical body is being rotated to remove the debris from an exterior portion of at least a portion of the dental implant device.

10. A method in accordance with claim 8, wherein the cylindrical body comprises providing a cylindrical body that includes an exterior surface to enable a user to grip and rotate the cylindrical body.

11. A method in accordance with claim 10, wherein the cylindrical body that includes an exterior surface comprises providing a cylindrical body that includes an exterior surface that includes a plurality of grooves.

12. A method in accordance with claim 8, wherein the at least one second cleaning projection (a) is a fin or a blade.

13. A method in accordance with claim 8, wherein the at least one second cleaning projection (b) comprises a plurality of cleaning rows and each cleaning row comprises a plurality of additional cleaning protrusions that each extend radially outward from the projection.

\* \* \* \* \*